United States Patent [19]

Harris et al.

[11] Patent Number: 5,242,379
[45] Date of Patent: Sep. 7, 1993

[54] ANKLE BRACE WITH FLOATING PIVOT HINGE

[75] Inventors: David P. Harris, Grand Rapids, Mich.; Michael E. Berkeley, Glenwood Springs, Colo.

[73] Assignee: Exoflex, Inc., Sunfish Lake, Minn.

[21] Appl. No.: 700,544

[22] Filed: May 15, 1991

Related U.S. Application Data

[63] Continuation-in-part of Ser. No. 547,595, Jul. 2, 1990, Pat. No. 5,094,232.

[51] Int. Cl.$^5$ ............................................. A61F 5/00
[52] U.S. Cl. ..................................... 602/27; 602/16; 602/65
[58] Field of Search ............... 128/80 H, 80 F, 80 R, 128/88, 166; 623/39, 47; 602/27, 62, 65, 14

[56] References Cited

U.S. PATENT DOCUMENTS

| | | | |
|---|---|---|---|
| 1,390,915 | 9/1921 | Loth | 623/39 |
| 1,737,897 | 12/1929 | Skoglund | 602/62 |
| 2,382,679 | 8/1945 | Tollman | |
| 2,485,036 | 10/1949 | Christopher | |
| 2,516,872 | 8/1950 | Hauser et al. | |
| 2,632,440 | 3/1953 | Hauser et al. | |
| 2,910,310 | 10/1959 | Mulac | |
| 3,779,654 | 12/1973 | Horne | 128/80 H |
| 3,826,251 | 7/1974 | Ross | |
| 3,970,083 | 7/1976 | Carrigan | 602/65 |
| 4,084,586 | 4/1978 | Hettick | 128/80 H |
| 4,136,404 | 1/1979 | Lange | |
| 4,187,844 | 2/1980 | Caprio, Jr. | 602/65 |
| 4,280,488 | 7/1981 | Polsky et al. | 602/65 |

(List continued on next page.)

FOREIGN PATENT DOCUMENTS 473487 6/1927 Fed. Rep. of Germany.
424467 12/1924 Fed. Rep. of Germany.

OTHER PUBLICATIONS

W. Muller, "The Knee," Springer-Verlag, Berlin, Heidelberg, New York 1983, pp. 8-13.
V. Frankel, "Basic Biomechanics of the Skeletal System," Lea & Febiger, Philadelphia 1980, pp. 113-125.

*Primary Examiner*—Richard J. Apley
*Assistant Examiner*—Lynne A. Reichard
*Attorney, Agent, or Firm*—Merchant, Gould, Smith, Edell, Welter & Schmidt

[57] ABSTRACT

An ankle brace for limiting flexing and pivoting movement of the ankle joint. The brace includes a soft resilient sock and a pair of brace panels positioned and retained over the sock on opposite sides of the ankle and foot. Each panel is formed by a pair of brace sections hinged together by a floating pivot axis hinge. The hinge includes a pair of juxtaposed hinge plates adapted to pivot and slide with respect to each other. One of the plates is secured to the ankle section of the brace and the other is secured to the foot section of the brace. Each plate defines a pivot face, with a concave groove defined in each face. The concave grooves are normally positioned at right angles with respect to each other when the pivot faces are juxtaposed. A single pivot bearing ball is positioned between the opposed pivot faces and retained in the concave grooves. A spring resiliently biases the hinge plates together against the ball pivot bearing. A second spring biases the plates for relative sliding movement. The pivot bearing ball and grooves provide a floating pivot axis for hinge rotation and sliding movement of the hinge plates, and thereby the brace sections, relative to each other. A post-injury sleeve is provided to cover the wearer's ankle after injury to provide some support thereto and/or to hold an ice pack against the swollen ankle. A kit for ankle support includes the ankle brace and a post-injury sleeve. A method for aiding the healing of an injured ankle includes the use of a post-injury sleeve and a brace.

8 Claims, 7 Drawing Sheets

U.S. PATENT DOCUMENTS

| | | |
|---|---|---|
| 4,320,747 | 3/1982 | Daniell, Jr. |
| 4,353,361 | 10/1982 | Foster |
| 4,361,142 | 11/1982 | Lewis et al. |
| 4,372,298 | 2/1983 | Lerman |
| 4,392,488 | 7/1983 | Will |
| 4,409,689 | 10/1983 | Buring et al. |
| 4,433,679 | 2/1984 | Mauldin et al. |
| 4,463,751 | 8/1984 | Bledsoe |
| 4,531,731 | 7/1985 | Law |
| 4,617,920 | 10/1986 | Carsalade |
| 4,620,532 | 11/1986 | Hauswerth |
| 4,637,382 | 1/1987 | Walker |
| 4,651,726 | 3/1987 | Holland .......................... 128/80 H |
| 4,688,559 | 8/1987 | Vito |
| 4,691,697 | 9/1987 | Arensdorf et al. |
| 4,697,583 | 10/1987 | Mason et al. |
| 4,724,847 | 2/1988 | Nelson ............................ 128/80 H |
| 4,727,863 | 3/1988 | Nelson ............................ 602/65 |
| 4,729,370 | 3/1988 | Kallassy ......................... 602/65 |
| 4,771,768 | 9/1988 | Crispin ........................... 128/80 H |
| 4,844,094 | 7/1989 | Grim ............................... 128/80 H |
| 4,869,267 | 9/1989 | Grim et al. ..................... 128/80 H |

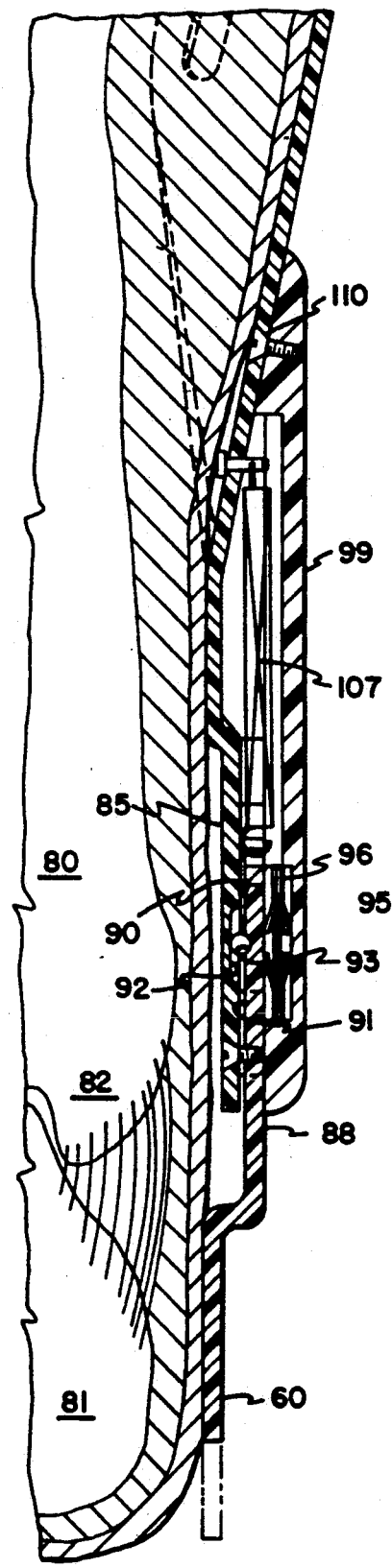
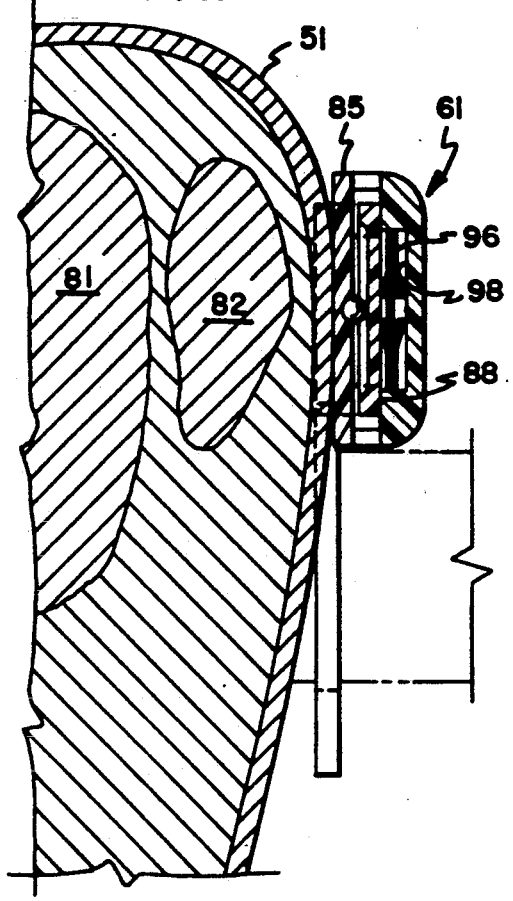
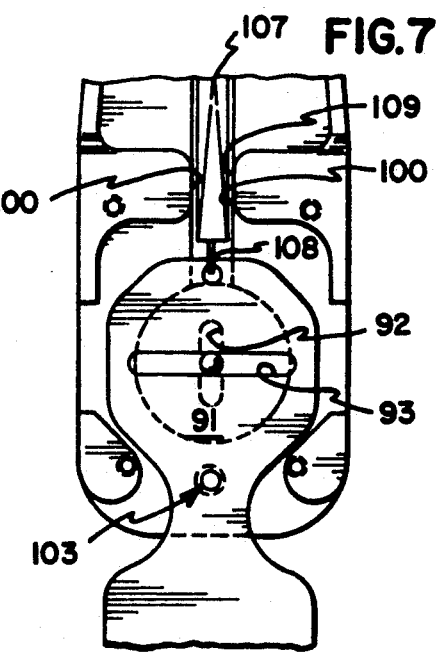

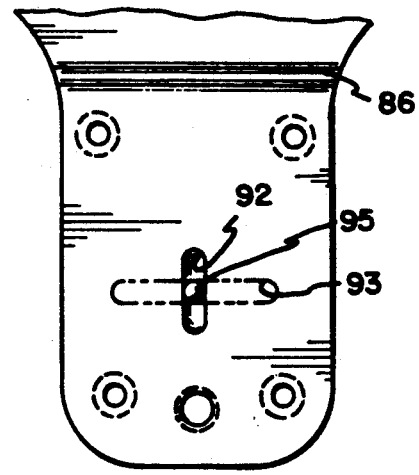
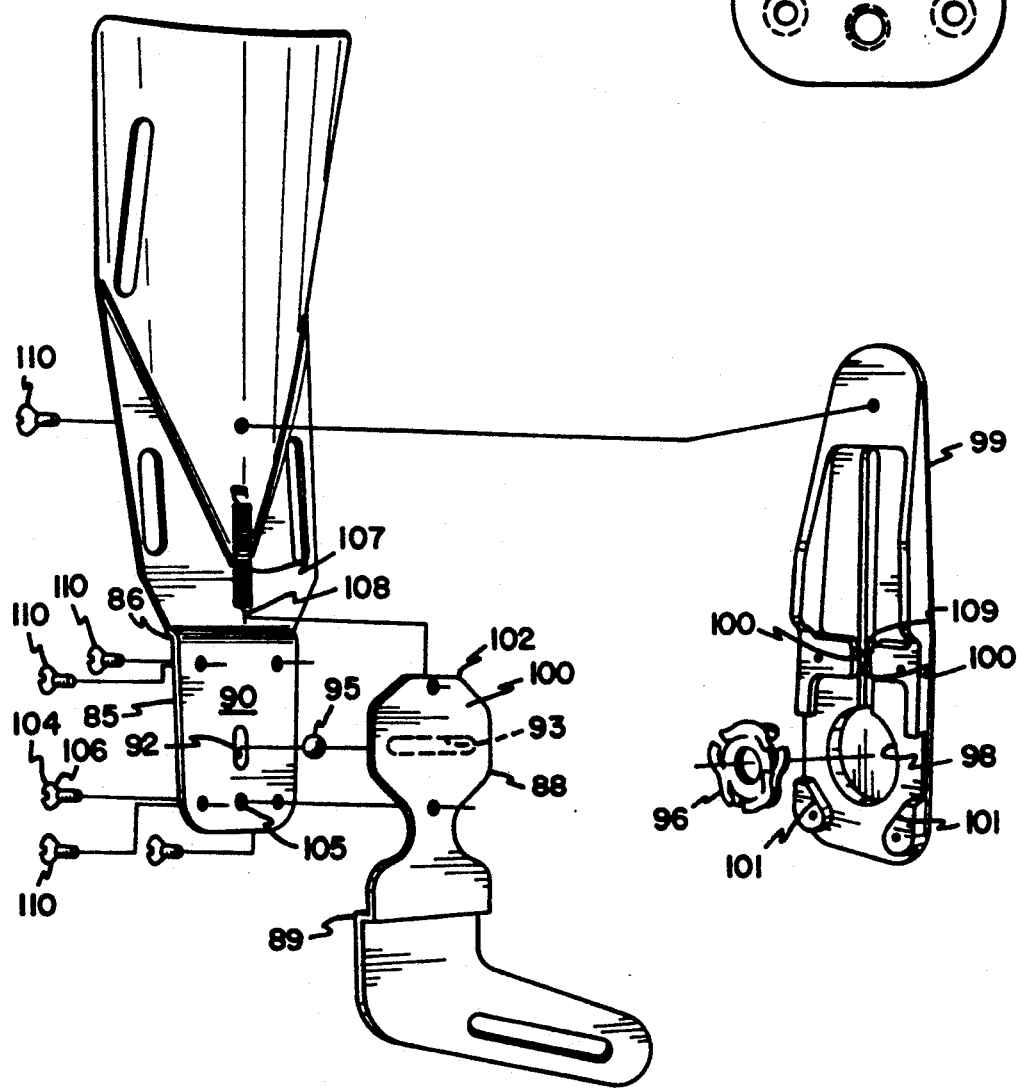

ANKLE BRACE WITH FLOATING PIVOT HINGE

This application is a continuation-in-part of U.S. Ser. No. 07/547,595, filed Jul. 2, 1990, now U.S. Pat. No. 5,094,232.

BACKGROUND OF THE INVENTION

1. Field of the Invention

The present invention relates to an ankle brace and more particularly to an ankle brace structure which uses floating pivot hinges. More specifically, the present invention relates to a hinged ankle brace structure for supporting an ankle and foot while permitting partial or limited movement thereof. The present invention further relates to a flexible sleeve that covers the wearer's ankle and is useable alone or in combination with the ankle brace to provide support and/or to hold a cold pack or the like against the wearer's ankle. Still further, the invention relates to a kit for supporting an ankle including an ankle brace and a flexible sleeve. The invention relates to a method of aiding the healing of an ankle using a post-injury sleeve and a brace.

2. Description of The Prior Art

Extensive studies have shown that the human knee and foot joints involve complex mechanisms which provide for extension and flexion movement as well as for rotary movement. These movements result from both a rotating and sliding movement as well as a pivoting movement in the knee and ankle joints. A detailed discussion of the ankle and foot joints appears in V. H. Frankel and M. Nordin, "Basic Biomechanics of the Skeletal System," Chapters 6 and 7, Lea & Febiger, Philadelphia, 1980.

A floating pivot hinge is described in detail in U.S. Pat. No. 4,938,206, issued Jul. 3, 1990, to Michael E. Berkeley, David P. Harris, and William C. McCune for "Floating Pivot Hinge and Knee Brace." The floating pivot hinge disclosed by Berkeley et al. is formed by a pair of juxtaposed hinge plates each having a pivot face in opposition to a pivot face on the juxtaposed plate with a concave groove in each of the faces. A pivot bearing ball is confined between the opposed faces and retained in the concave grooves. A spring, such as a Belleville spring, finger spring, disk spring, or leaf spring, biases the hinge plates together when the pivot bearing ball is positioned in the opposed grooves between the plates. The pivot bearing ball provides a floating pivot axis for hinge rotation of the hinge plates. The ball and concave grooves allows the hinge plates simultaneously to slide and pivot relative to each other. The pivot axis floats between the hinge plates, depending on the degree of pivoting and sliding movement in a wearer's knee joint as a result of flexion thereof.

OBJECTS OF THE INVENTION

It is the principal object of the present invention to provide an improved ankle brace which allows partial normal flexing and pivoting movement of the ankle and foot joint, while restraining abnormal twisting, flexing or extension of the ankle and foot.

Another object of the present invention is to provide an ankle brace of the foregoing character with a hinge construction which tracks the complex movement of the ankle with respect to the foot and leg.

It is a further object of the present invention to provide an ankle brace of the foregoing character which provides for limited movement of the wearer's foot.

It is another object of the present invention to provide a flexible sleeve that can be used alone or in combination with the ankle brace, to provide support for the ankle and/or to securely hold a cold pack or heat pack against the wearer's ankle.

It is another object of the present invention to provide a kit for use in supporting a wearer's ankle, with the kit including an ankle brace and a sleeve.

It is another object of the present invention to provide a method for aiding the healing of an injured ankle including the use of a post-injury sleeve and an ankle brace.

Other objects and advantages of the present invention will become apparent from the following description taken in connection with the accompanying drawings.

SUMMARY OF THE INVENTION

An ankle brace incorporating a floating pivot point or pivot axis hinge is formed by a pair of opposed brace panels adapted to be secured to the wearer's leg on opposite sides of an ankle, foot and lower leg. For this purpose, the lower leg, ankle and foot heel portion are first partially covered by a sock formed of a soft resilient material such as a foam rubber material having a smooth inner surface formed by a soft knit, cloth, and a loop pile exterior surface. A zipper or seam is provided in the sock for convenience in covering the leg, ankle and foot. The zipper is depicted in FIG. 3 as being to the side of the wearer's leg. The zipper may, however, be positioned at any other position in the sock, for instance along the top.

A brace panel is positioned on each opposite side of the lower leg, ankle and foot encased within the sock. The brace panels are each provided with fabric hook fasteners which readily engage with the loop pile of the sock to enable the user to readily position the brace panels against the foot and ankle.

The brace panels are further tightly secured to the wearer's leg, ankle and foot by an upper leg strap which extends through slots in the brace and wraps around the calf to hold the brace tightly thereto. A second strap secures the brace panels to the leg and ankle at a point just above the ankle, while a third strap wraps around the foot to secure the brace panels tightly to the wearer's foot.

Each brace panel is articulated into two panel sections joined by a floating pivot hinge. The upper calf or ankle section is secured to the wearer's calf and ankle by the calf and ankle straps, while the lower foot section is secured to the wearer's foot by a strap which extends around the sole and arch of the foot. The straps are preferably secured to the panels so that the panels are held tightly and relatively immovably in place with respect to the leg and foot.

The pivot hinge comprises a floating pivot hinge of the type generally described in U.S. Pat. No. 4,938,206. In the ankle brace modification, the floating pivot hinge is formed by a pair of juxtaposed hinge plates one of which is secured to the upper or ankle panel section and the other is secured to the lower or foot panel section. A concave groove is recessed into each plate, one of the grooves being generally horizontal with respect to the foot and the other being generally vertical with respect to the foot so that the grooves extend generally perpendicularly to each other when the foot and ankle are in the relaxed position. The vertical groove is shorter by approximately one-half than the relatively longer horizontal groove. Both grooves are concave and provide a deeper central portion and a shallower remote portion. A single ball pivot hinge is mounted between the plates in the grooves and provides a pivot axis about which the hinge panels and brace sections coupled thereto can rotate.

One of said panels defines a peripheral housing which serves to restrict the hinge panels and the brace panel sections coupled thereto with respect to each other. A spring such as a Belleville spring, or a finger spring biases the two plates together trapping the ball pivot hinge between them while a second biasing spring adds a force sufficient to position the hinge plates so that the ball is at the central depressed portion of each groove when the wearer's foot is relaxed. The biasing means provided in the embodiments described may be formed by a portion of the brace panels, such as by formation of leaf springs formed by injection molding. The hinge construction is defined in more detail in U.S. Pat. No. 4,938,206.

More specifically, the present invention comprises an ankle brace for a wearer's foot and ankle. The brace comprises a soft resilient sock covering the wearer's foot and ankle and a pair of brace panels secured to opposite sides of the wearer's leg and ankle. Each brace panel comprises an ankle section and a foot section. A calf strap is adapted to extend around the wearer's calf to hold said brace thereto. An ankle strap is adapted to extend around the wearer's ankle to hold said brace thereto, and a foot strap is adapted to extend around a wearer's foot to hold the brace thereto. A floating pivot axis hinge rotatably connects the respective ankle and foot brace panel sections of each pair. Each hinge comprises a pair of juxtaposed hinge plates adapted to pivot and slide with respect to each other, one of said plates being secured to the ankle brace section and the other being secured to the corresponding foot brace section. Each hinge plate has a pivot face in opposition to a pivot face on the juxtaposed plate, and a concave groove is defined in each of the faces. The concave grooves are arranged perpendicularly with respect to each other to define a generally horizontal groove and a generally vertical groove, the length of the generally horizontal groove being longer than the length of the generally vertical groove. Each groove has a deeper point and a shallower point. A single pivot bearing ball is positioned between the opposed plate faces and is retained in the concave grooves. A spring resiliently biases the hinge plates together against the pivot bearing ball when the ball is positioned in the opposed grooves between the opposing faces. The pivot bearing ball is positioned at the deeper point of each groove when the grooves are perpendicularly aligned, corresponding to the normal relaxed position of the wearer's foot.

When mounted on a wearer's leg and ankle the ankle brace precludes all but a limited scope of movement of the foot and ankle with respect to the leg. The edges of the grooves restrict the range of motion of the pivot axis, and thereby restrict motion of the wearer's foot. For instance, the top edge of the grooves limit rotation of the foot about an axis extending lengthwise through the foot. Rotational movement of the brace panels with respect to each other is restricted by limiting the pivoting movement of the hinge panels through inter-engaging stops formed on the respective hinge plates. As the wearer's foot pivots, flexes and points, the hinge tracks the swinging and sliding movement of the ankle joint. Further as the wearer walks, the hinge restricts the natural twisting movement of the ankle. Thus the brace provides for restrained and supported but limited movement of the foot and ankle.

DESCRIPTION OF THE DRAWINGS

In the drawings, in which like reference numerals are used throughout to identify corresponding elements through several views.

FIG. 5 is an enlarged section view taken substantially in the plane of line 5—5 on FIG. 2.

FIG. 6 is an enlarged section view taken substantially in the plane of line 6—6 on FIG. 2.

FIG. 7 is a section view taken substantially in the plane of line 7—7 on FIG. 5.

FIG. 8 is a section view taken substantially in the plane of line 8—8 on FIG. 5.

FIG. 9 is an exploded partial perspective view of the ankle brace shown in FIG. 4.

FIG. 12 is an enlarged diagrammatic x-ray view of an ankle bone or talus and leg bone or tibia showing relative sliding and pivoting movement there between.

DESCRIPTION OF THE PREFERRED EMBODIMENT

Figure 11:
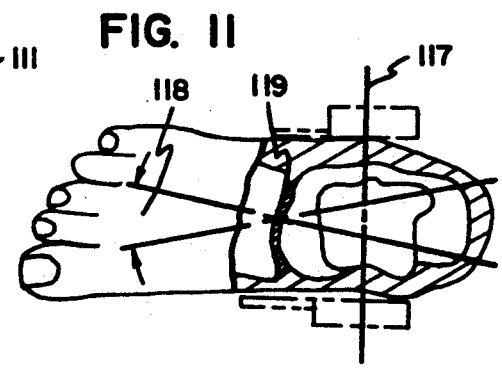
FIG. 11 is a diagrammatic x-ray representation of a foot showing the angle range of movement of the foot during twisting.
Figure 12:
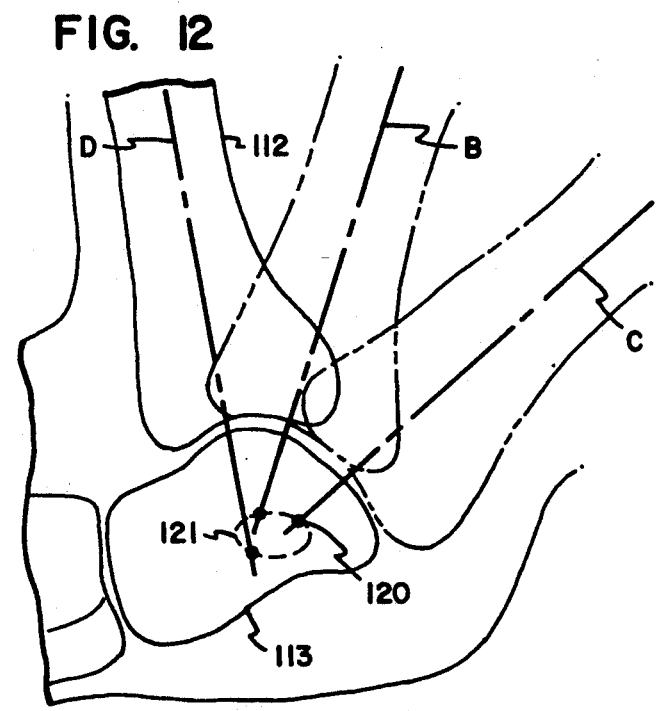
Figure 13:
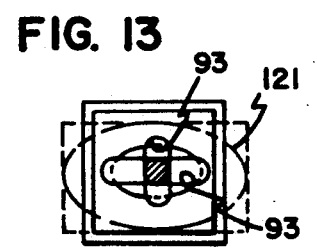
FIG. 13 is a diagrammatic representation of the hinge plates of the ankle brace shown in FIG. 1 relative to the locus of pivoting movement shown in FIG. 12A.

An ankle brace 50 embodying the present invention is shown in the drawings. Referring to FIGS. 1–4 the ankle brace 50 is formed by a soft yieldable foam sock 51 adapted to be inserted over the wearer's foot, ankle and lower leg, and a pair of spaced brace panels 52, 53 positioned over the sock 51 adjacent the inner and outer sides of the foot and ankle. The brace panels 52, 53 are securely held to the leg by appropriate straps which may include an upper calf strap 55, an intermediate ankle strap 56 and a lower foot strap 57. Each brace panel 52, 53 is formed in two sections, an upper ankle section 59 and a lower foot section 60, and the sections are joined by a floating pivot hinge 61. The floating pivot hinges 61 track the natural flexing and twisting movements of the ankle within predetermined limits. The brace 50 thus provides support for the ankle joint while allowing only a limited range of movement of the foot and ankle, as shown in FIGS. 11, 12 and 13.

Figure 1:
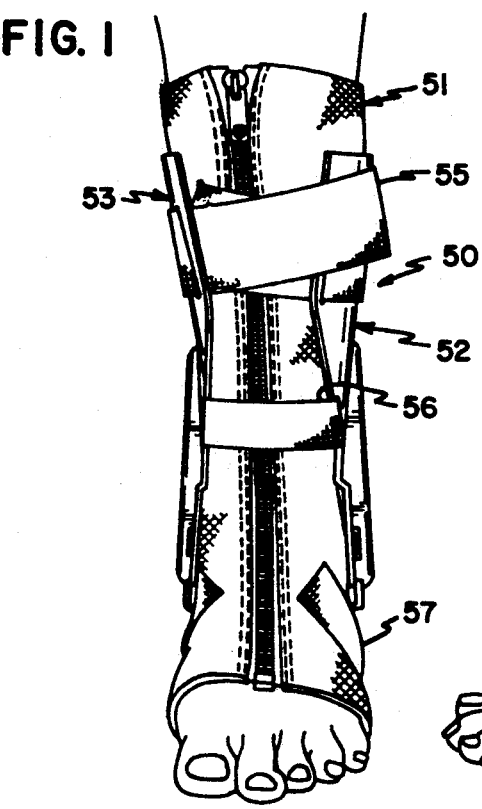
FIG. 1 is a front elevation view of an ankle brace embodying the present invention positioned on a wearer's leg.
Figure 2:
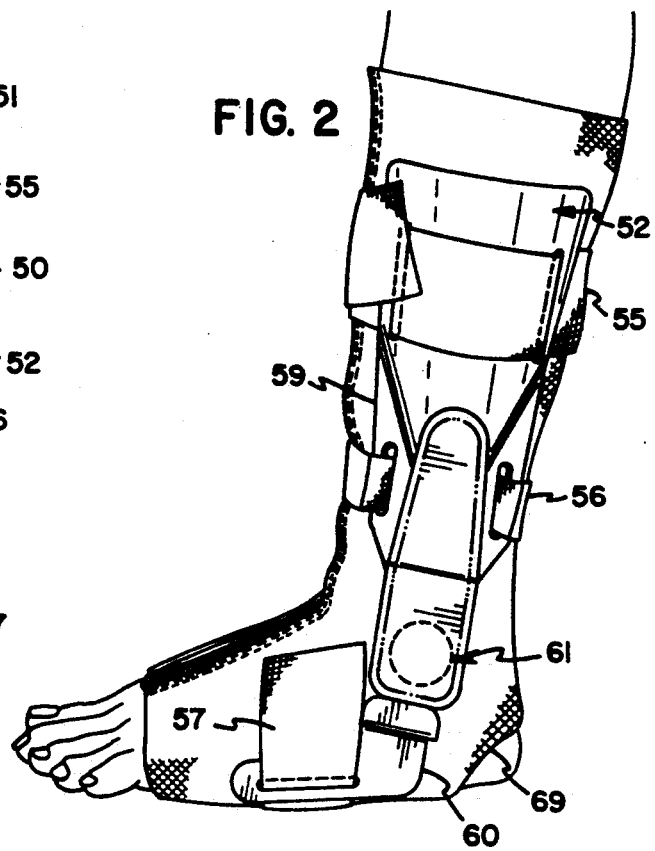
FIG. 2 is a right side elevation view of the ankle brace shown in FIG. 1.
Figure 3:
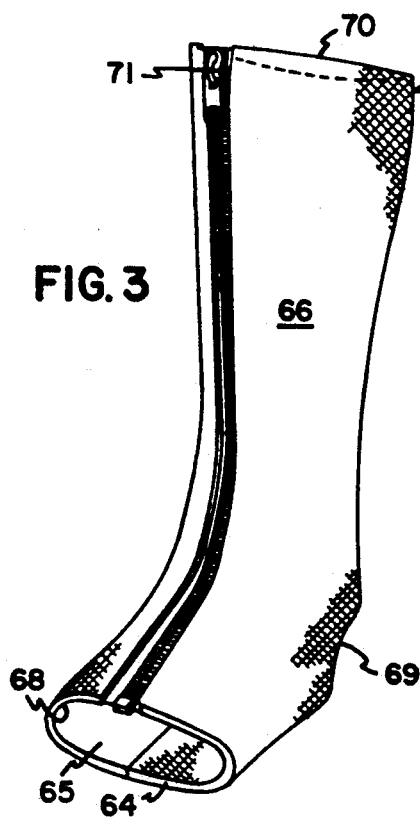
FIG. 3 is an isometric view of a sock utilized in association with the ankle brace shown in FIG. 1.

The preferred soft flexible sock 51 shown in FIG. 3 comprises a foam layer 64 covered on its inner surface with a smooth soft knit fabric 65, and on its outer surface with a loop pile fabric 66. A toe opening 68, heel opening 69 and leg opening 70 are provided and a zipper 71 may be provided on the side of the sock to facilitate application of the sock to the wearer's foot. In addition to the straps 55, 56 and 57, hook pile patches 72 are secured to the inner surfaces of the brace panels at spaced points therealong for releasable engagement with the loop pile surface 66 of the sock 51. These hook pile patches secure the brace panels to the sock to prevent movement of the brace panels relative to the sock as well as to assist the securing of the brace to the wearer's foot and leg. The brace panels thus stick to the sides of the sock allowing the wearer to secure the fastening straps 55, 56 and 57. As an alternative to having the exterior surface of the sock be loop pile fabric, it is contemplated that loop pile strips or patches be provided on the exterior surface of the sock which may be of any desirable fabric or material.

Further, in an alternative embodiment, it is contemplated that the sock include pockets sized, shaped, and positioned to receive and snugly hold the brace panels therein, with or without the assistance of hook and loop fastening patches or strips.

Figure 4:
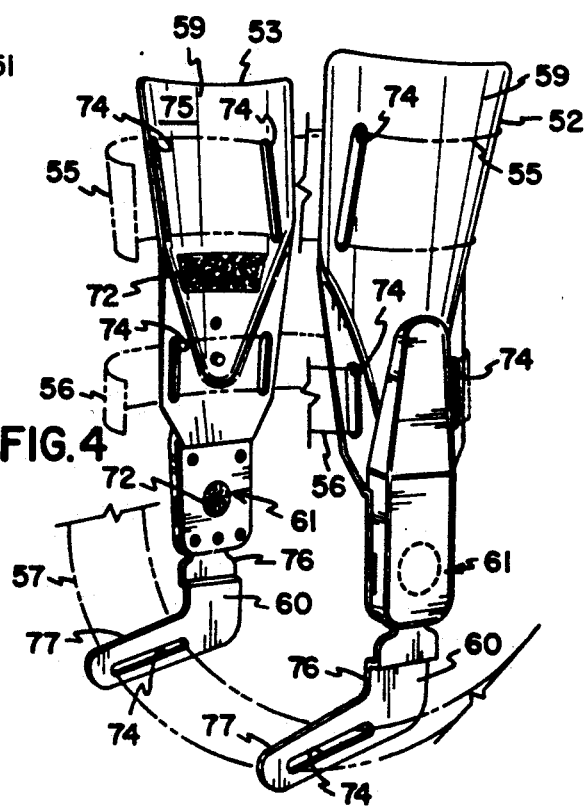
FIG. 4 is an isometric view of portions of the ankle brace shown in FIG. 1.

The brace panels 52, 53 are essentially a mirror image of each other, as shown in FIG. 4. The brace may be sized for a particular foot and ankle by providing means for adjustably securing the straps to the respective brace panels. Alternatively, the brace panels 52 and 53 may differ from each other somewhat to achieve further advantageous support for the ankle and control over its movement. For example, the grooves on the brace panel 52 may be sized differently from the grooves on the brace panel 53.

The brace panels are, as indicated above, formed in two sections, an upper calf section 59 and a lower foot section 60 joined by the floating pivot hinge assembly 61. The upper calf section 59 is formed as a slightly curved plate or panel defining a plurality of slots 74 for receiving and retaining the straps 55, 56. The calf panel 59 defines an inner surface 75 which is curved to fit snugly against the sock 51 and the wearer's lower calf.

The foot panel 60 is generally L-shaped, defining a vertical portion 76 and a generally horizontal foot portion 77. The latter defines a strap slot 78 for receiving the foot strap 57. The foot strap 57 is desirably secured to the horizontal portion 77 to prevent slipping of the strap with respect thereto.

The straps may use any appropriate fastening mechanism, the preferred fastener being a hook and loop pile. This enables the straps not only to be secured to each other but also to grip the inner sock 51 thereby providing additional strength to the brace and enabling it to be secured tightly to the wearer's leg and foot without restricting circulation. The straps, brace panels and sock provide a unitary construction for supporting the foot and ankle.

The use of the sock to attach the brace panels to the ankle is a preferred embodiment of the present invention. In alternative embodiments, the brace panels may be incorporated into a shoe, or a skate, or may be unitary with the sock structure.

The floating pivot hinge assembly 61 is shown in detail in FIGS. 5-9 inclusive. This floating pivot hinge involves the concept described and claimed in U.S. Pat. No. 4,938,206. Referring to FIG. 5 of the drawings, the hinge construction is shown in association with a tibia 80 and talus 81 forming an ankle joint. The sock 51 surrounds the ankle, and the brace calf section or panel 59 and foot section or panel 60 are positioned adjacent the tibia and talus respectively. The hinge assembly 61 is positioned adjacent the ankle joint and ankle bone 82.

The hinge assembly 61 is formed by a hinge plate 85 extending from and integral with the upper ankle panel section 59 of the brace panel 52. The hinge plate 85 is off-set from the panel section 59 by a shoulder 86 which provides for clearance between the hinge plate 85 and the ankle bone 82.

A second hinge plate 88 is integral with and extends from the lower foot section 60 of the ankle brace panel 52 and likewise is off-set therefrom by a shoulder 89. The hinge plates 85, 88 define opposed faces or surfaces 90, 91 respectively into which are cut concave recesses such as grooves 92, 93 respectively. A ball bearing pivot 95 is retained in the grooves 92, 93 and provides a floating pivot joint between the hinge plates 85, 88. As shown particularly in FIGS. 8 and 9, one concave groove 92, in a hinge plate 85, is generally vertical while the other concave groove 93, in the other hinge plate 88, is generally horizontal with respect to the tibia. When the hinge plates are placed in face-to-face relationship, the grooves are generally perpendicular to each other. It should be understood that either groove could be placed in either face.

The hinge plates 85, 88 are held in facing juxtaposed relationship with the pivot bearing ball trapped therebetween in the grooves by a biasing spring 96 retained in a recess 98 in a housing cover 99 secured to the inner hinge plate 85. The spring acts on the back surface 100 of the outer hinge plate 88 and biases the outer hinge plate 88 against the pivot ball 95. The spring 96 may be of a flat washer configuration such as a Belleville spring, finger spring, or similar circular leaf spring.

For constraining relative movement between the hinge plates, while allowing the hinge plates to slide and twist with respect to each other about a floating pivot point provided by the pivot ball 95, one hinge plate 85 includes a peripheral wall 100 and abutment members 101 adapted to engage the peripheral edges 102 of the other hinge plate 88. Within the limits defined by the wall 100 and abutments 101, the hinge plates can twist and slide relative to each other in a full floating relationship about the floating pivot point defined by the pivot ball 95.

It may be desirable in some instances for the brace 50 to prohibit movement of the ankle altogether. For example, in the days immediately following an injury, it may be desirable for the ankle to be substantially immobilized. To accumulate this need, a preferred embodiment of the brace includes structure 103 which selectively inhibits hinging movement of the hinge plates with respect to one another. For instance, in the embodiment illustrated in FIG. 9, a screw 104 is provided which extends through one brace panel and into a corresponding foot panel. Most desirably, the head of the screw is accessible from the exterior of the brace to allow the adjustment of the screw without having to remove the brace from the wearer's ankle. That is, in the embodiment shown, the screw 104 passes through the brace panel and into the foot panel, with the brace panel preferably having a countersunk recess 105 to receive the head 106 of the screw, such that the screw head 106 is exposed on the exterior of the brace 50.

In most preferred embodiment, the screw 104 can be tightened selectively such that it provides resistance to, but does not necessarily prohibit, relative movement between the brace panel and the foot panel 60. In such an arrangement, the screw 104 preferably can be tightened sufficiently prevent or prohibit relative movement of the calf panel 59 with respect to the foot panel 60.

Because of the nature of the foot and ankle joint, it is desirable to bias the foot panel section 60 upwardly, and for this purpose a biasing spring 107 is secured between the hinge plate 88 secured to the foot section 60 and the ankle section 59. The housing cover 99 encloses the biasing spring 107 to prevent it from becoming tangled in the straps or external matter. A hinge post 108 extends upwardly from the hinge plate 88 through an aperture or passage 109 in the retaining wall 100 where it is connected to the biasing spring 107. The cover 99 is secured to the upper brace section by appropriate fasteners 110.

Figure 10:
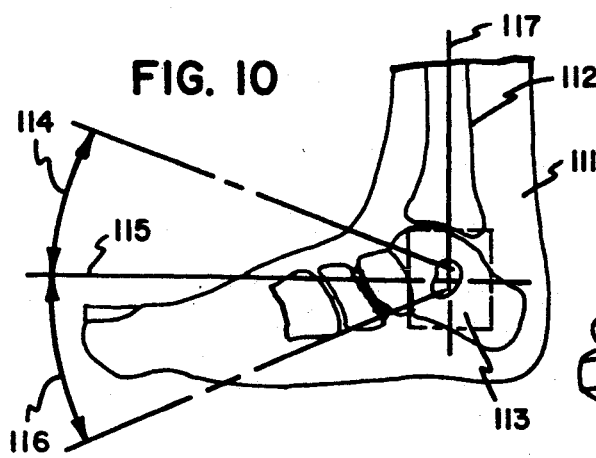
FIG. 10 is a diagrammatic representation of an elevation x-ray view of a foot showing the angle range of movement of the foot during flexing and pointing.

The constraining walls 100, 101 on inner hinge plate 85 co-act with the peripheral edge of the outer hinge plate 88 to provide for limited twisting and sliding movement between the two hinge plates. In a preferred embodiment, this peripheral edge is generally octagonal, but in alternative embodiments may have a different shape, such as elliptical to achieve desired control over and limitation of movement of the ankle. The twisting and sliding movement between the plates is further restricted by the relationship of the concave grooves and single pivot ball bearing 95. The pivoting, sliding, twisting motion controlled by the ankle brace is schematically depicted in FIGS. 10-13 which illustrate a foot 111, tibia 112 and astragalus or talus 113. As shown in FIG. 10, the foot 111 can flex through a vertical angle 114 above the horizontal 115 and point through a vertical angle 116 relative to the horizontal 115. The vertical axis 117 extends through the foot although the swinging movement of the foot from side to side through a horizontal angle 118 is about a reference point 119 spaced from the vertical axis 117 through the tibia as shown in FIG. 11.

Figure 12A:
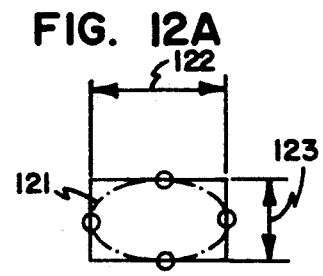
FIG. 12A is a diagrammatic representation of the center pivot points of movement shown in FIG. 12.
Figure 13A:
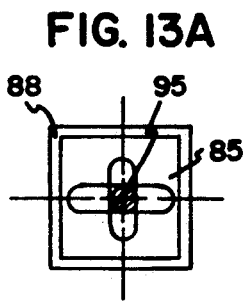
FIGS. 13A, 13B, 13C and 13D are diagrammatic representations of the relative movement of the hinge plates of the ankle brace shown in FIG. 1.
Figure 13B:
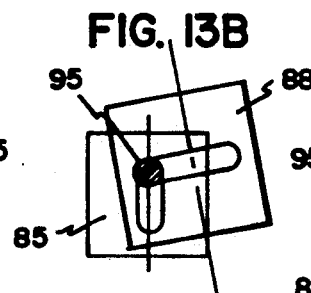
Figure 13C:
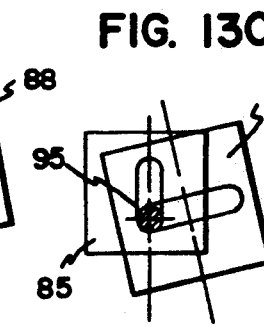
Figure 13D:
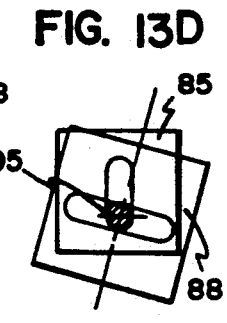

The sliding movement of the tibia 112 with respect to the talus 113 is illustrated in FIG. 12. As the tibia swings and pivots relative to the talus, the pivot point 120 defines a generally J-shaped path 121 which may be extrapolated to an oval as shown in FIG. 12A. This path 121 is longer, 122, than it is deep, 123. The comparison of the path 121 to the hinge plates and concave slots 92, 93 is depicted in FIG. 13. FIGS. 13A-13D depict the movement of the floating pivot point defined by the ball bearing 95 as it tracks the pivoting movement of the ankle joint. Referring to FIG. 12, the foot and tibia extend from one extreme C when the foot is at full point through an intermediate position B when the foot is partially pointed to a further extreme position D when the foot is flexed. This position of the foot corresponds to the hinge positions as shown in FIGS. 13B, 13C and 13D respectively. FIG. 13A illustrates the foot in a normal or relaxed position as shown in FIG. 10.

Figure 14:
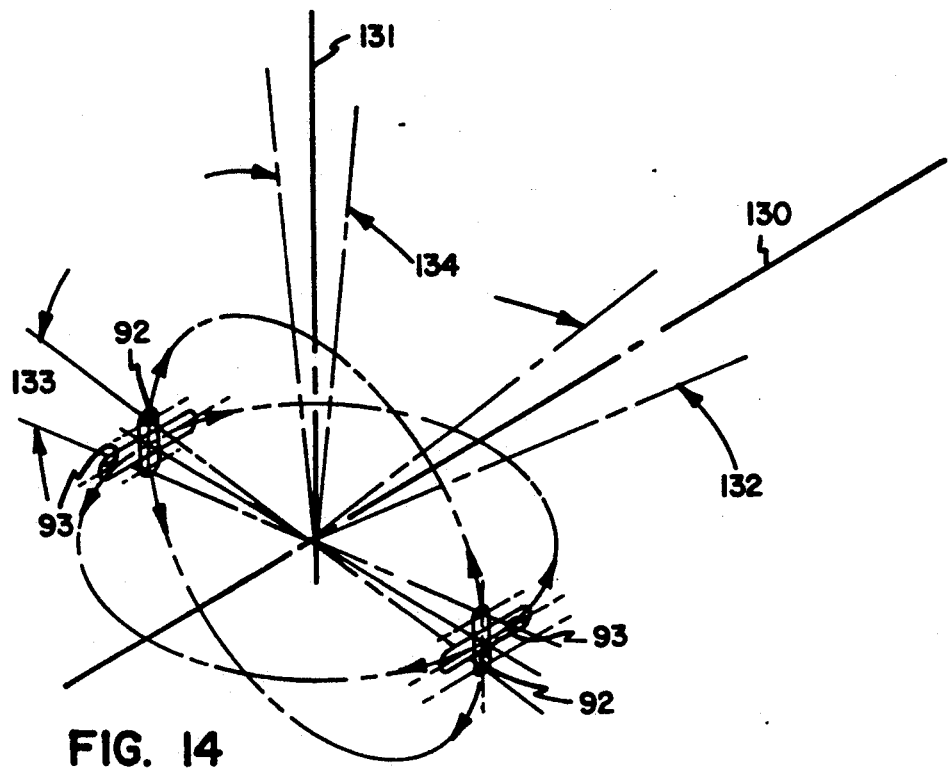
FIG. 14 is a diagrammatic representation of the locus of points of movement of a foot, ankle and leg joint in relationship to the hinge plates shown in FIG. 1.
Figure 15:
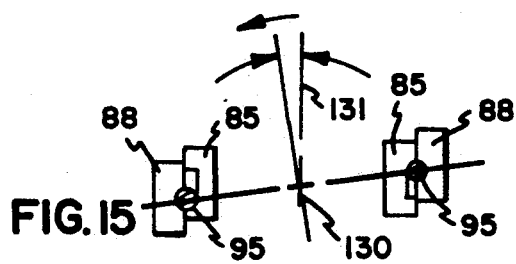
FIGS. 15, 16, 17, 18, 19, and 20 are diagrammatic representations of the relative movement of the hinge plates during flexing and twisting of an ankle joint.
Figure 18:
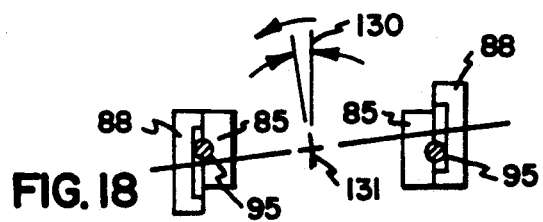
Figure 16:
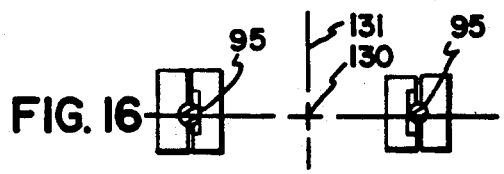
Figure 19:
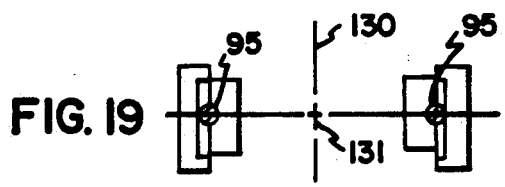
Figure 17:
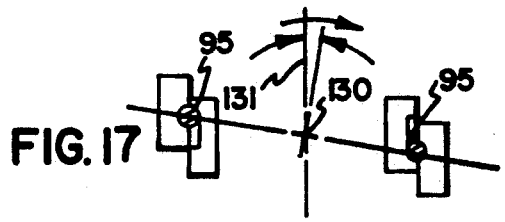
Figure 20:
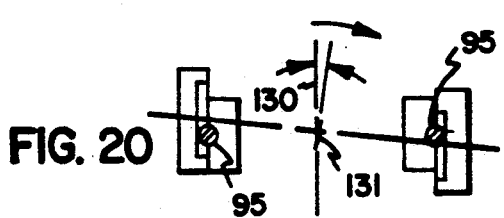

The movement of the foot is further schematically illustrated in FIG. 14 which illustrates schematically both pointing and flexing as well as twisting about a vertical and a horizontal axis. FIGS. 15-20 illustrate the twisting movement of the foot about a horizontal axis resulting from effective side to side movement of the foot. In FIG. 14 there is illustrated a horizontal axis of movement 130 and a vertical axis 131. The foot can twist about either of these axes within the limits provided by the pivot hinge when the ankle brace is secured to the foot. The twisting of the foot and ankle about a vertical axis parallel to the tibia is illustrated by the included angle 132. Side to side twisting of the foot about a horizontal axis 130 is illustrated by the included angle 133. Pointing and flexing of the foot about a horizontal axis perpendicular to the longitudinal axis is illustrated by the included angle 134. The various positions of the hinge plates are schematically demonstrated in FIGS. 15-20. FIGS. 15, 16, and 17 demonstrate a side to side twisting action about the longitudinal axis of the foot. FIGS. 18-20 illustrate the pivoting of the foot in the horizontal plane about the vertical axis parallel to the tibia.

The invention further contemplates the possible use of the concave recess or depression in one of the hinge plate faces or surfaces with the pivot ball retained in a depression or hole in the surface of the other hinge plate. The concave depression or recess may be circular, defining a conical inclined plane surface, or generally oval or rectangular in configuration with surfaces sloping from a deepest central portion outwardly at varying degrees of slope to the peripheral edges of the depression. The configuration must be such that the hinge tracks the natural complex pivoting, sliding and twisting movement of the joint being supported.

The interface between the brace panels and the wearer's skeleton via the sock provides advantages. Because the floating pivot hinge applied herein is able to follow the natural movement of an ankle joint so closely, it is particularly desireable for the brace panels to be firmly connected to the skeleton. Of course, the brace would not be directly fixed to the skeleton in most applications. Further, the brace panels cannot be directly affixed to the skin. The sock assists the connection of the brace panels to the skeleton, by providing a stabilizing surface which gloves the outer surface of the ankle, to which the brace panels can be directly, firmly attached. In this manner, the brace panels and the sock have a uni-body construction and the "slop" or looseness of connection between the brace panels and the skeleton is less than it would be without the sock, and therefore the brace can more effectively support desired movement in the ankle and prevent undesirable movement.

Figure 21:
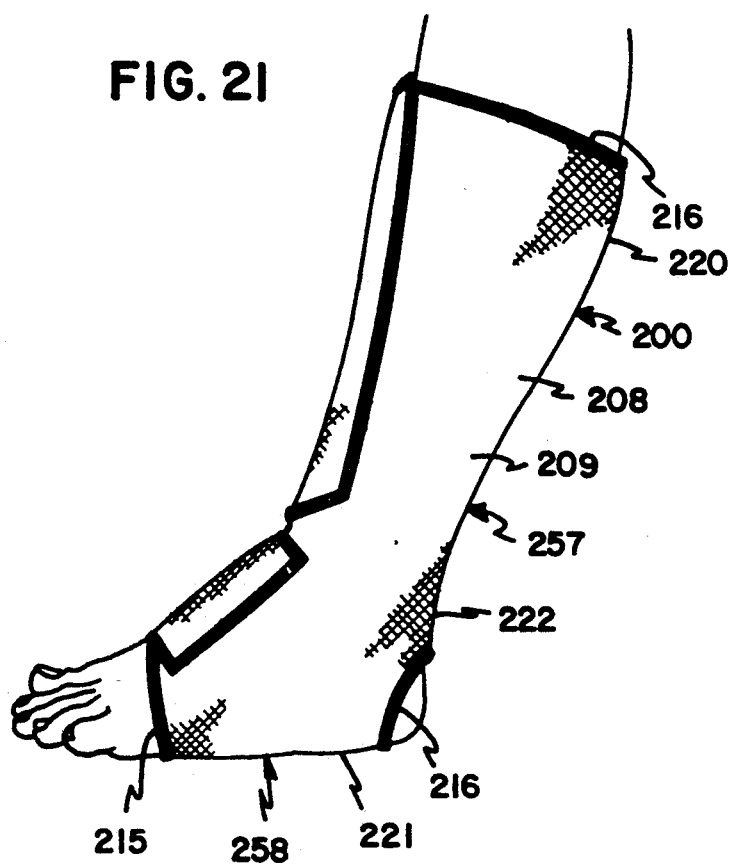
FIG. 21 is an elevated perspective view of the sleeve of FIG. 20, shown in its tubular form, wrapped around a wearer's ankle.
Figure 22:
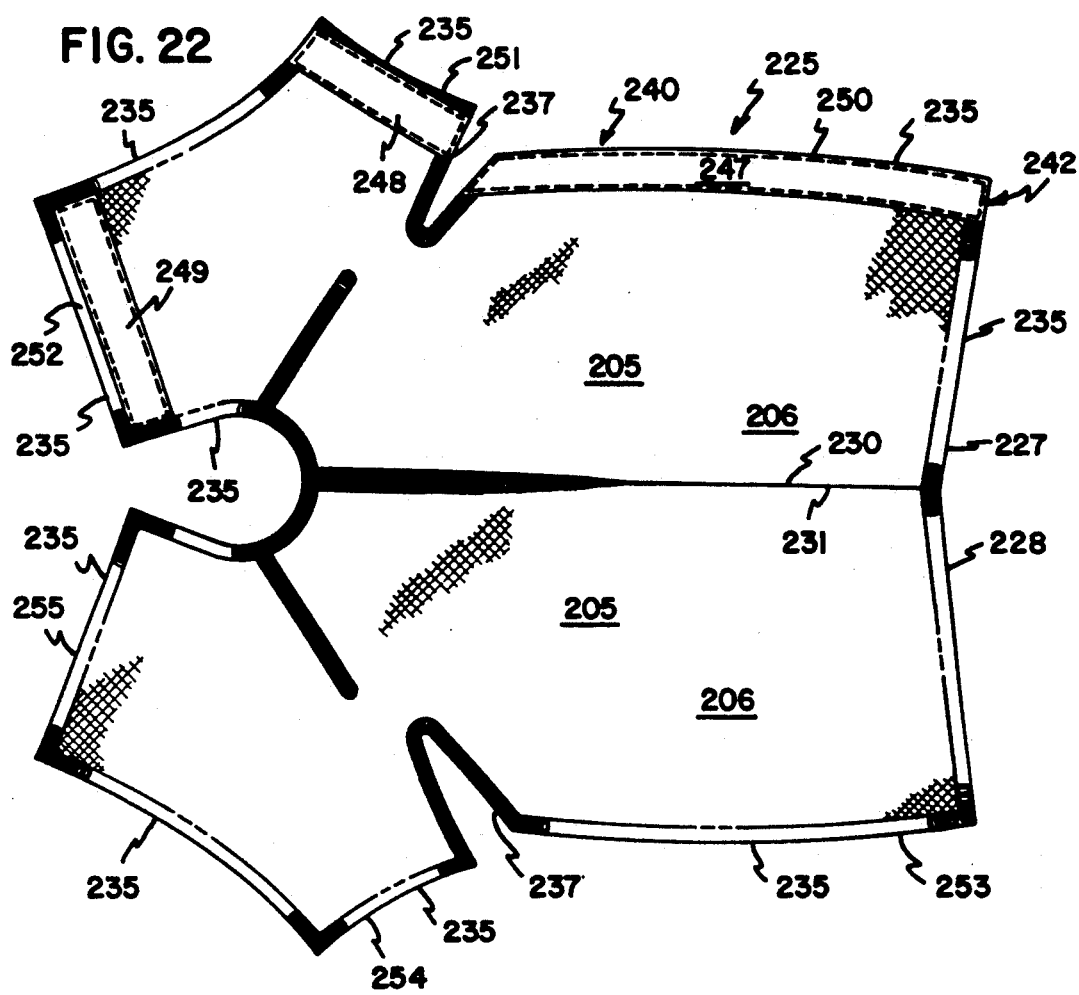
FIG. 22 is an elevated perspective view of a two-dimensional blank form from which the flexible sleeve, shown in FIG. 21, is formed.
Figure 23:
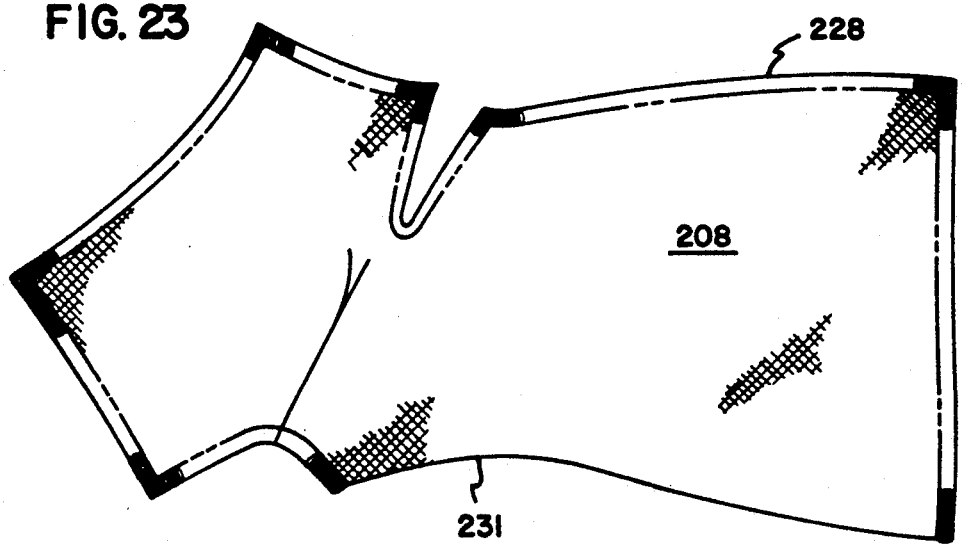
FIG. 23 is an elevated plan view of half of a blank form like that illustrated in FIG. 22.

As illustrated in FIGS. 21-23, the preferred embodiment of a brace arrangement according to the present invention includes a sleeve 200 that is preferably separable from the ankle brace and from the flexible sock. The sleeve 200 can be used to provide some support to an ankle after injury. For instance, the sleeve can be used when swelling prohibits use of the brace itself. Further, that the sleeve 200 can be used to hold an ice pack or other cold-inducing object against the injured ankle. The cold-inducing object is preferably positioned between the ankle or calf and the interior surface of the sleeve 200. In another embodiment, the sleeve 200 includes an interior pocket sized and shaped to receive a cold-inducing object therein, with the interior side of the pocket being made of relatively non-insulating material. Thus, the sleeve 200 is sized to accommodate a swollen ankle and/or an ice pack.

Preferably the sleeve is made of a material that provides relatively high insulation against the ambient air temperature. The flexible sleeve 200 preferably comprises a foam layer covered on its inner surface 205 with a smooth knit fabric 206, and on its outer surface 208 with a loop pile fabric 209. Advantages achieved by providing loop pile fabric on the outer surface will be understood from the discussion below. It is to be understood, however, that other fabrics may be used for each of the inner and outer surfaces 205, 208. A toe opening 215, heel opening 216, and a leg opening 217 are provided.

The sleeve has generally three portions: a calf portion 220, a foot portion 221, and an ankle portion 222 therebetween. In use, the calf portion 220 generally covers the wearer's calf or the lower portion of the wearer's calf. The foot portion 221 substantially covers the wearer's foot. The calf portion 220 and the foot portion 221 are attached to or integral with one another, thereby forming an ankle portion 222 therebetween which generally covers the wearer's ankle.

The preferred sleeve embodiment 200 is formed of a generally two-dimensional blank form or pattern 225. The blank 225 is shaped as shown in FIG. 22.

It can be understood that the blank is formed of two substantially mirror-image half sections 227 and 228, attached to one another along longitudinal back edges 230, 231 such as by a sewn seam. In the position illustrated in FIG. 22, the blank 225 is substantially flat or planar; however, because of curvature in these edges 230, 231 seam that will be discussed below, the blank does not lie perfectly flat in this open position.

As illustrated in FIG. 22, an outer peripheral edge 235 defines the shape of the blank. The outer peripheral edge 235 includes notches 237, 238 in the ankle portion 222 between the calf portion 220 and the foot portion 221 to allow the blank 225 to wrap around the ankle without excessive bulk of material about the ankle.

Fastening structure 240 is provided to selectively and releasably fix mating peripheral edges of the blank together to form the generally tubular sleeve 200, as shown in FIG. 21. The preferred fastening structure 240 includes loop and pile fasteners 242 along the mating peripheral edges of the half sections 227, 228. Preferably, one surface 205 or 208 of the sleeve is loop pile. Hook pile patches or strips are secured to a surface on one or more mating edges of the blank, to selectively and releasably engage a portion of the loop pile surface 209. As noted above, in the embodiment illustrated in FIG. 22, the inner surface of the sleeve is loop pile. Strips or patches of hook pile are attached along several edges 247, 248 and 249 on the interior surface 205 of the sleeve. More specifically, in the embodiment illustrated, a hook pile strip 247 is attached to the interior surface 205 along the relatively long, generally vertical edge 250 of the blank 225 along the calf portion 220. Another hook pile strip 248 is attached to the interior surface 205 along a generally horizontal top edge 251 of the foot portion 221. Yet another hook pile strip 249 is attached to the interior surface 205 along a generally horizontal bottom edge 252 of the foot portion 221.

Most preferably the sleeve 200 is formed from the blank 225 by placing the wearer's leg against the interior surface 205 of the sleeve and wrapping the sleeve 200 around the wearer's calf, ankle and foot. Hook pile strip 247 engages opposite edge portion 253; hook pile strip 248 engages opposite edge portion 254 along the top of the wearer's foot; and hook pile strip 249 engages opposite edge portion 255 along the bottom of the wearer's foot. In this manner the blank 225 illustrated in FIG. 22 becomes the sleeve illustrated in FIG. 21. More specifically, a tubular calf covering 257 is formed when edges 250 and 253 are joined. A tubular foot covering 258 is formed when edges 251 and 254 are joined and when edges 252 and 255 are joined. The ankle is covered by portions of both the calf covering and the foot covering.

As noted above, the longitudinal seam 260 joining the longitudinal back edges 230, 231 of the half sections 227, 228, is curved. This is apparent with reference to FIG. 23. This contour allows the sleeve to fit more snugly about the ankle and therefore to provide greater support and/or to hold an ice-pack or the like more closely against the ankle.

It is preferable that one surface of the sleeve be of loop pile, so that it can fasten to the hook pile strips. Because the entire surface can be used to fasten the mating edge thereto, the sleeve can conform to a range of foot, ankle and calf sizes. Further, the size of the wearer's ankle may increase and decrease with swelling so it is advantageous to have the size of the sleeve easily variable so that the wearer need not purchase a number of sleeves of various sizes.

It is to be understood, however, that if neither surface of the sleeve is loop pile, loop pile strips can be attached along the appropriate edges. Further, it is contemplated that fastening structure 240 other than hook and loop materials be used. For instance, zippers, hook and eyes, snaps or the like may be used. The hook and pile arrangement described above and illustrated in FIGS. 21-23 is advantageous because it allows the user to easily adjust the size of the sleeve. This is desirable, for instance, when the wearer's ankle changes diameter due to an increase or decrease in swelling.

Another aspect of the present invention is a kit for ankle support including, in a most preferred embodiment, a brace 50, like that illustrated in FIG. 1-9 and discussed above, and a flexible sleeve 200, like that illustrated in FIGS. 21-23 and discussed above. In use, the sleeve 200 can be used immediately or shortly after injury to provide some support to the ankle and, if desired, to hold a cold pack or cold-inducing object, against the wearer's skin to reduce swelling. Later, when it is desirable to have the ankle move within the confines of the brace 50, the brace 50 can be used with or without the sleeve 200. If the sleeve is used with the brace 50, it is positioned to surround the brace to, for instance, prevent the surfaces of the brace from catching on other objects, or to hold a cold pack or the like against the braced ankle.

Another aspect of this invention is a method of aiding the healing of an injured ankle by using the post-injury sleeve relatively shortly after injury to support the ankle and/or to hold a cold-inducing object, such as an ice pack, against the ankle. After swelling is reduced, the ankle brace can be applied to prevent undesired movement of the ankle and to accommodate desired movement of the ankle.

While a certain illustrative embodiment of the present invention has been shown in the drawings and described in detail in the specification, it should be understood that there is no intention to limit the invention to the specific form and embodiments disclosed. On the contrary, the intention is to cover all modifications, alternative constructions, equivalents and uses falling within the spirit and scope of the invention as expressed in the appended claims.

What is claimed is:

1. An ankle brace adapted to limit flexing and pivoting movement of the ankle joint and foot comprising:

a pair of brace panels adapted to be positioned and retained on opposite sides of a wearer's leg and ankle, each brace panel comprising a pair of brace sections hinged together by a floating pivot axis hinge for restraining and limiting the movement of an ankle and foot supported thereby;

said hinge including a pair of juxtaposed hinge plates adapted to pivot and slide with respect to each other, each said plate having a pivot face in opposition to a pivot face on the juxtaposed plate, a concave recess in at least one of said faces, and a single pivot bearing ball positioned between said opposed faces and retained in said concave recess;

said pivot bearing ball thereby providing a floating pivot axis for hinge rotation of said hinge plates relative to each other, said concave recess allowing said hinge plates to slide relative to each other and simultaneously pivot relative to each other about said floating pivot axis defined by said ball.

2. An ankle brace according to claim 1, wherein said brace further includes means to inhibit hinging movement of said brace sections with respect to one another.

3. An ankle brace according to claim 2, said brace further comprising means for selectively inhibiting pivoting and sliding movement of said hinge plates relative to each other.

4. An ankle brace according to claim 3, wherein said inhibiting means includes a screw extending through one of said hinge plates and frictionally against the other, thereby creating resistance to relative movement between said hinge plates.

5. A method of aiding the healing of an injured ankle comprising the steps of:

a) applying a flexible post-injury sleeve after sustaining an injury to the ankle; said sleeve having interior and exterior surfaces;

b) providing a cold-inducing object between the wearer's skin and the interior surface of said sleeve to reduce and prevent swelling;

c) applying an ankle brace after swelling has sufficiently decreased; said ankle brace including a pair of brace panels adapted to be positioned and retained on opposite sides of a wearer's leg and ankle, each brace panel comprising a pair of brace sections hinged together by a floating pivot axis hinge for restraining and limiting the movement of an ankle and foot supported thereby.

6. An ankle brace adapted to limit flexing and pivoting movement of the ankle joint and foot comprising:

a pair of brace panels adapted to be positioned and retained on opposite sides of a wearer's leg and ankle, each brace panel comprising a pair of brace sections hinged together by a floating pivot axis hinge for restraining and limiting the movement of an ankle and foot supported thereby;

said hinge including a pair of juxtaposed hinge plates adapted to pivot and slide with respect to each other, each said plate having a pivot face in opposition to a pivot face on the juxtaposed plate, a concave recess in at least on of said faces, a single pivot bearing ball positioned between said opposed faces and retained in said concave recess, means for resiliently biasing said hinge plates together against said pivot bearing ball when said ball is positioned between said opposing faces, said pivot bearing ball thereby providing a floating pivot axis for hinge rotation of said hinge plates relative to each other, said concave recess allowing said hinge plates to slide relative to each other and simultaneously pivot relative to each other about said floating pivot axis defined by said ball; and said brace further including means to inhibit hinging movement of said brace sections with respect to one another.

7. An ankle brace according to claim 6, said brace further comprising means for selectively inhibiting pivoting and sliding movement of said hinge plates relative to each other.

8. An ankle brace according to claim 7, wherein said inhibiting means includes a screw extending through one of said hinge plates and frictionally against the other, thereby creating resistance to relative movement between said hinge plates.

* * * * *